United States Patent
Arramon et al.

(10) Patent No.: US 11,160,672 B2
(45) Date of Patent: Nov. 2, 2021

(54) ROBOTIC SYSTEMS AND METHODS FOR DISTRACTION IN INTERVERTEBRAL DISC PROSTHESIS IMPLANTATION

(71) Applicant: Simplify Medical Pty Ltd, Paddington (AU)

(72) Inventors: Yves Arramon, Sunnyvale, CA (US); David Hovda, Mountain View, CA (US); Michael Sherman, Memphis, TN (US)

(73) Assignee: Simplify Medical Pty Ltd, Paddington (AU)

(*) Notice: Subject to any disclaimer, the term of this patent is extended or adjusted under 35 U.S.C. 154(b) by 136 days.

(21) Appl. No.: 16/578,968

(22) Filed: Sep. 23, 2019

(65) Prior Publication Data

US 2020/0093614 A1    Mar. 26, 2020

Related U.S. Application Data

(60) Provisional application No. 62/735,710, filed on Sep. 24, 2018.

(51) Int. Cl.
*A61B 17/58* (2006.01)
*A61B 17/60* (2006.01)
(Continued)

(52) U.S. Cl.
CPC ............ *A61F 2/4611* (2013.01); *A61B 34/10* (2016.02); *A61F 2/4657* (2013.01);
(Continued)

(58) Field of Classification Search
None
See application file for complete search history.

(56) References Cited

U.S. PATENT DOCUMENTS

| 6,226,548 B1 | 5/2001 | Foley et al. |
| 6,340,363 B1 | 1/2002 | Bolger et al. |
| (Continued) | | |

FOREIGN PATENT DOCUMENTS

| EP | 2381858 B1 | 11/2018 |
| JP | 2017536909 A | 12/2017 |
| (Continued) | | |

OTHER PUBLICATIONS

International Search Report and Written Opinion for PCT/AU2019/000116 dated Jan. 10, 2020.

*Primary Examiner* — Sameh R Boles
(74) *Attorney, Agent, or Firm* — Hoffman Warnick LLC

(57) ABSTRACT

Systems and methods for robotically distracting a disc space are provided for implantation of an intervertebral prosthetic disc. The system includes a 3D modeling system for creating a 3D model of first and second vertebra adjacent the disc space and identifying positions of the first and second vertebrae. A robotic distractor precisely opens the disc space just large enough to receive a selected intervertebral disc. A computing system stores and processes the 3D model and the positions of the first and second vertebrae before and after distraction. A surgeon interface on the computing system allows the surgeon to select an intervertebral disc prosthesis to be implanted and a desired distraction distance or force to be achieved.

15 Claims, 2 Drawing Sheets

(51) Int. Cl.
  *A61F 2/00* (2006.01)
  *A61F 2/46* (2006.01)
  *A61B 34/10* (2016.01)

(52) U.S. Cl.
  CPC ...... *A61F 2/4684* (2013.01); *A61B 2034/105* (2016.02); *A61B 2034/108* (2016.02); *A61F 2/4603* (2013.01); *A61F 2002/4633* (2013.01); *A61F 2002/4658* (2013.01); *A61F 2002/4666* (2013.01); *A61F 2002/4681* (2013.01)

(56) References Cited

U.S. PATENT DOCUMENTS

| | | | |
|---|---|---|---|
| 7,542,791 B2 | 6/2009 | Mire et al. | |
| 7,567,834 B2 | 7/2009 | Clayton et al. | |
| 7,575,599 B2 | 8/2009 | Villiers et al. | |
| 7,585,326 B2 | 9/2009 | De Villiers et al. | |
| 7,637,913 B2 | 12/2009 | De Villiers et al. | |
| 7,753,956 B2 | 7/2010 | De Villiers et al. | |
| 8,043,295 B2 | 10/2011 | Reed et al. | |
| 8,100,979 B2 | 1/2012 | Felt et al. | |
| 8,206,449 B2 | 6/2012 | Jansen et al. | |
| 8,337,508 B2 | 12/2012 | Lavallee et al. | |
| 8,394,144 B2 | 3/2013 | Zehavi et al. | |
| 8,685,035 B2 | 4/2014 | De Villiers et al. | |
| 8,764,833 B2 | 7/2014 | De Villiers et al. | |
| 8,840,629 B2 | 9/2014 | Bonutti | |
| 8,897,514 B2 | 11/2014 | Feikas et al. | |
| 8,992,580 B2 | 3/2015 | Bar et al. | |
| 9,011,544 B2 | 4/2015 | Arramon et al. | |
| 9,125,680 B2 | 9/2015 | Kostrzewski et al. | |
| 9,351,846 B2 | 5/2016 | De Villiers et al. | |
| 9,545,233 B2 | 1/2017 | Sirpad et al. | |
| 9,782,229 B2 | 10/2017 | Crawford et al. | |
| 10,034,711 B2 | 7/2018 | Greenwald et al. | |
| 2006/0084986 A1 | 4/2006 | Grinberg et al. | |
| 2007/0198022 A1 | 8/2007 | Lang et al. | |
| 2008/0195081 A1 | 8/2008 | Moll | |
| 2009/0234217 A1* | 9/2009 | Mire ............ | G16H 50/50 600/407 |
| 2009/0299477 A1 | 12/2009 | Clayton et al. | |
| 2011/0306873 A1 | 12/2011 | Shenai et al. | |
| 2014/0378999 A1 | 12/2014 | Crawford et al. | |
| 2015/0032164 A1 | 1/2015 | Crawford et al. | |
| 2015/0366624 A1 | 12/2015 | Kostrzewski et al. | |
| 2017/0265774 A1 | 9/2017 | Johnson et al. | |
| 2018/0014891 A1 | 1/2018 | Krebs et al. | |
| 2018/0110573 A1 | 4/2018 | Kostrzewski | |
| 2018/0125598 A1 | 5/2018 | Mcafee | |
| 2018/0199951 A1 | 7/2018 | Chappuis et al. | |
| 2018/0221008 A1 | 8/2018 | Todorov et al. | |

FOREIGN PATENT DOCUMENTS

| | | |
|---|---|---|
| WO | WO-2010064234 A2 | 6/2010 |
| WO | WO-2016131903 A1 | 8/2016 |
| WO | WO-2016154356 A1 | 9/2016 |
| WO | WO-2018167246 A1 | 9/2018 |
| WO | WO-2020061611 A1 | 4/2020 |

* cited by examiner

ROBOTIC SYSTEMS AND METHODS FOR DISTRACTION IN INTERVERTEBRAL DISC PROSTHESIS IMPLANTATION

CROSS-REFERENCE TO RELATED APPLICATIONS

This application claims the benefit of U.S. Provisional No. 62/735,710, filed Sep. 24, 2018, the entire content of which is incorporated herein by reference.

BACKGROUND OF THE INVENTION

1. Field of the Invention

The present invention relates to medical devices and methods. More specifically, the invention relates to intervertebral prosthetic discs and systems and methods for robotically distracting a disc space for implantation of an intervertebral prosthetic disc.

Back pain takes an enormous toll on the health and productivity of people around the world. According to the American Academy of Orthopedic Surgeons, approximately 80 percent of Americans will experience back pain at some time in their life. On any one day, it is estimated that 5% of the working population in America is disabled by back pain.

Common causes of back pain are injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs. With age, intervertebral disks begin to shrink. In some cases, they may collapse completely and cause the bones to rub against one another. This is also referred to as osteoarthritis.

When a damaged intervertebral disc causes a patient pain and discomfort, surgery is often required. Typically, surgical procedures for treating damaged intervertebral discs involve discectomy (partial or total removal of a disc), often followed by interbody fusion of the superior and inferior vertebrae adjacent to the disc or implantation of an intervertebral prosthetic disc. Fusion is most commonly achieved by implantation of a cage or spacer together with bone graft material to promote bone growth to fuse the adjacent vertebrae together. Oftentimes, pins, rods, screws, cages and/or the like are placed between the vertebrae to act as support structures to hold the vertebrae and bone graft material in place while the bones permanently fuse together. Spinal fusion eliminates motion between the vertebrae. Fusion is an option when motion is the source of pain.

An alternative to spinal fusion which doesn't limit patient mobility is intervertebral disc replacement (TDR), also called total disc arthroplasty. The TDR procedure involves removing the natural disk from between the vertebrae and replacing it with and artificial disc prosthesis. Several types of intervertebral disc prosthesis are currently available. For example, one type of intervertebral disc prosthesis includes upper and lower prosthesis plates which locate against and engage the adjacent vertebral bodies and a mobile core positioned between the plates. The core has upper and lower convexly curved surfaces and the plates have corresponding, concavely curved recesses which cooperate with the curved surfaces of the core. This allows the plates to slide over the core to allow spinal movement to take place.

Typical drawbacks of the known intervertebral disc prosthesis include insufficient resistance to wear and tear, restricted range of motion, undesirable contact between plates causing potential wear, excessive disc height not appropriately matched to patient anatomy and/or insufficient ability of the prosthesis to adhere to vertebral bone. These drawbacks have been acknowledged and new intervertebral disc prosthesis are being developed which have improved properties. However, the speed and precision of the intervertebral disc prosthesis surgical procedure could be improved for optimal performance.

Therefore, a need exists for improved intervertebral disc prosthesis implantation techniques. Ideally, such improved techniques would reduce or eliminate improperly placed prostheses and improved performance and pain relief for patients. At least some of these objectives will be met by the inventions described herein.

2. Description of the Background Art

A variety of intervertebral disc prosthesis designs and methods of implanting are described in described in U.S. Pat. Nos. 7,442,211; 7,531,001; 7,575,599; 7,585,326; 7,637,913; 7,753,956; 8,206,449; 8,685,035; 8,764,833; 9,011,544 and 9,351,846, each of which is incorporated herein by reference in its entirety.

BRIEF SUMMARY OF THE INVENTION

A surgical method for distraction of a disc space for implantation of an intervertebral disc prosthesis comprises identifying positions of first and second vertebrae and generating and storing a three-dimensional (3D) model of the first and second vertebrae in a computing system. A size of an intervertebral disc prosthesis to be implanted between the first and second vertebrae is determined, and distractor pins are inserted in the first and second vertebrae in a known trajectory.

The first and second vertebrae are distracted with a computer controlled robotic distractor which precisely opens the disc space sufficiently (just large enough) to receive the intervertebral disc prosthesis of the selected size.

A robotic system for distraction of a disc space for implantation of an intervertebral disc prosthesis includes a 3D modeling system for creating a 3D model of first and second vertebra adjacent the disc space and identifying positions of the first and second vertebrae and generating and storing position data for the positions of the first and second vertebrae. A robotic distractor is configured to precisely open the disc space just large enough to receive a selected intervertebral disc. A computing system stores and processes the 3D model and the positions of the first and second vertebrae before and after distraction. A surgeon interface on the computing system is configured to allow the surgeon to select an intervertebral disc prosthesis to be implanted and a desired distraction distance.

BRIEF DESCRIPTION OF THE DRAWINGS

The novel features of the invention are set forth with particularity in the appended claims. A better understanding of the features and advantages of the present invention will be obtained by reference to the following detailed descrip

DETAILED DESCRIPTION OF THE INVENTION

Positioning of an intervertebral disc prosthesis properly in the spine is an important part of a successfully total disc arthroplasty (TDR) procedure. The position of the implant in the intervertebral space can influence the range of motion, implant behavior and clinical result. Potential improper positions include discs not placed far enough posterior in the disc space due to insufficient distraction or mobility of the disc space. Surgeon experience, surgeon training, use of imaging modalities and patient anatomy are all factors which can influence accuracy of disc space distraction and disc placement.

In traditional disc arthroplasty procedures, the disc space between two vertebrae where the disc prosthesis is to be implanted is prepared for insertion of the prosthetic disc by removal of the natural disc, bone cutting and other preparation of the bone surfaces and distraction of the disc space. Distraction of the disc space is performed to restore disc height and gain access to the disc space for complete removal of the natural disc and insertion of the disc prosthesis. However, traditional manual distraction techniques using distraction forceps and/or Caspar distractors and pins do not provide precision and rely entirely on the surgeon expertise to perform proper distraction.

Robotic distraction as described herein can prevent over distraction of the disc space which can overstretch and overstress the surrounding structures causing patient pain and suboptimal performance of the intervertebral disc replacement. One consequence of over distraction of the disc space is nerve root tension which can cause pain. Controlled robotic distraction can distract and hold open the vertebral space at a precise amount of distraction force or a precise spacing determined so that the selected spacing will precisely accommodate a selected disc prosthesis and reduce forces on the disc prosthesis as it is inserted. Controlled distraction which precisely matches the vertebrae spacing to the disc prosthesis height can prevent damage to the prosthesis features or coatings. Robotic distraction can also assist in selecting a proper disc size for the anatomy of a patient. Controlled robotic distraction when used for determining the precise amount of distraction desired under a given distraction load allows the selection of the proper disc size to be used to maintain an optimal disc space height.

Figure 1:
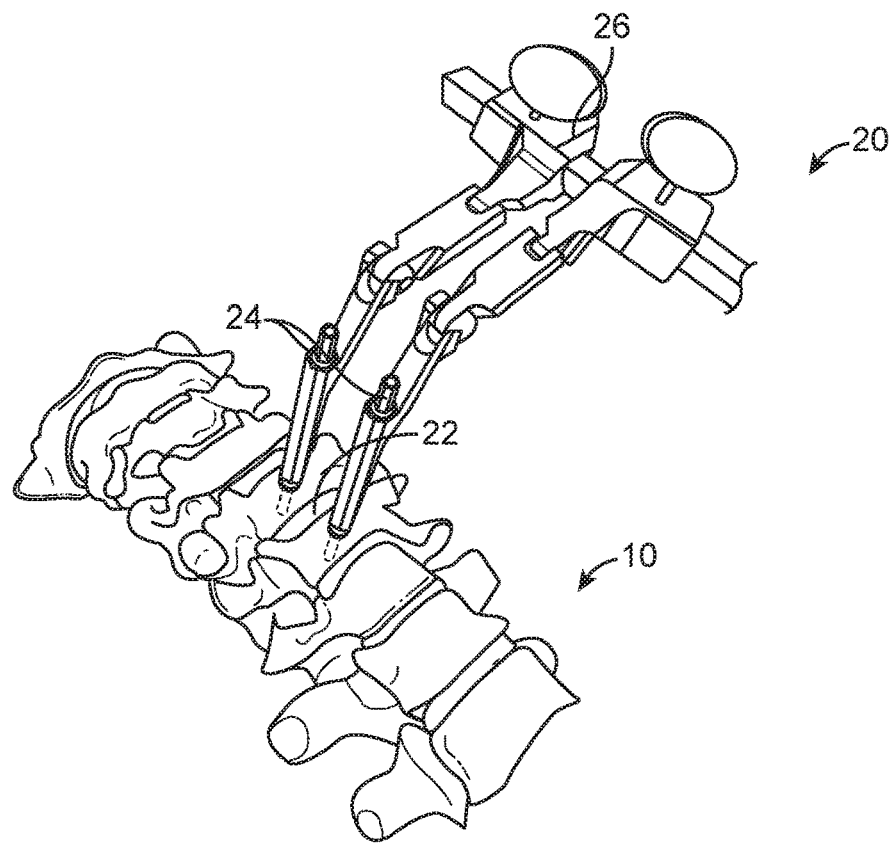
- FIG. 1 is a perspective view of a spine and a traditional manual Caspar-type spinal distractor.

FIG. 1 illustrates a cervical spine 10 with a traditional manual Caspar distractor 20 positioned to distract a space 22 between two adjacent vertebrae. A Caspar distractor system, as shown in FIG. 1, includes two Caspar pins 24 protruding from the upper and lower vertebral bodies and lying along the midline of the vertebrae. A handle 26 or handles of the Caspar distractor are located off of the midline so that the midline of the vertebral bodies and disc space are accessible during preparation of the disc space and insertion of the disc prosthesis or trials into the disc space 22.

Figure 2:
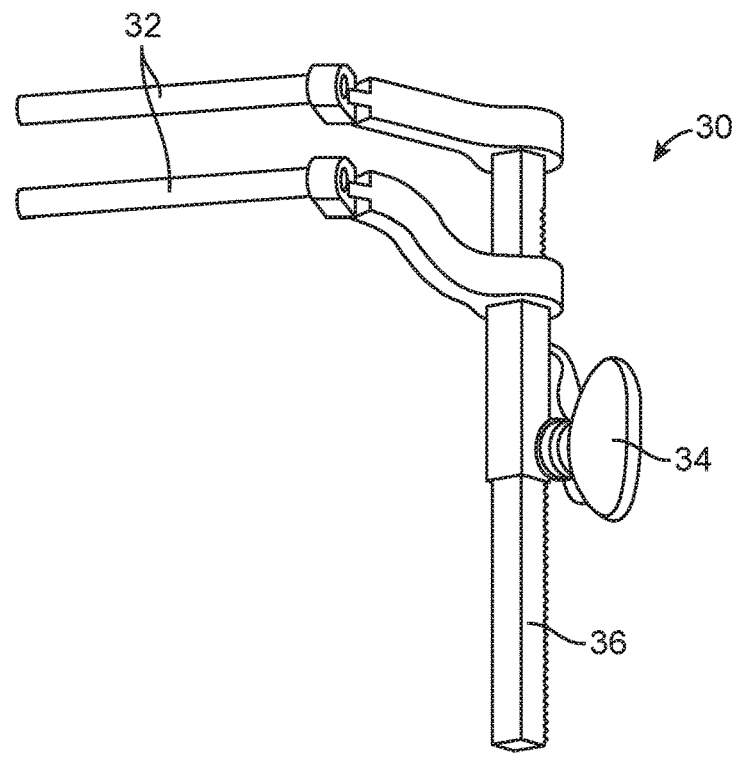
FIG. 2 is a perspective view of a traditional manual Caspar-type spinal distractor.

FIG. 2 shows an alternative Caspar distractor 30 having parallel distractor tubes 32 configured to be received over Caspar pins inserted into the vertebrae. A manual ratchet mechanism 36 is provided for moving the tubes in a parallel arrangement by rotation of a distractor handle 34.

Manual distraction of the disc space in preparation for insertion of a disc prosthesis is a multi-step process involving several steps of removing natural disc tissue, cutting or shaping bone and inserting trial implants. Between these preparation steps the distraction of the vertebrae may be adjusted a number of times to achieve a desired distraction. This trial and error preparation of the disc space extends the surgery time and requires repeated X-ray exposure as each time the surgeon removes bone or other tissue and fits a trial implant they check the fit on X-ray or fluoroscopy. An experienced surgeon learns to distract the vertebrae and fit the implant in an efficient manner. However patient anatomy can vary causing further difficulty in correctly distracting the disc space and implanting a disc prosthesis. A robotic distraction system can distract the two vertebrae with a computer controlled robotic distractor which precisely opens the disc space just large enough to receive an intervertebral disc prosthesis of a selected size.

Robotic and automated systems and methods for distracting vertebrae for an intervertebral disc implant as described herein can significantly improve intervertebral disc prosthesis placement by preventing both over distraction and under distraction. Automatic distraction systems can also reduce surgery time and provide more uniform results. In one robotic system, a robotic distractor is used in combination with an imaging system which produces a 3D model of the surgical site to allow the surgeon to control the robotic distractor according to a precise surgical plan.

The robotic distraction system can include a single midline distractor or two distractors on either side of the midline. Generally, a single midline distractor, such as shown in FIG. 1 is used in anterior cervical procedures where forces are lower. Two lateral mounted distractors are often used in lumbar procedures where forces are higher and vertebrae are larger to more easily accommodate additional distractor pins. However, for improved control of distraction two robotic distractors are shown for either cervical or lumbar procedures.

Figure 3:
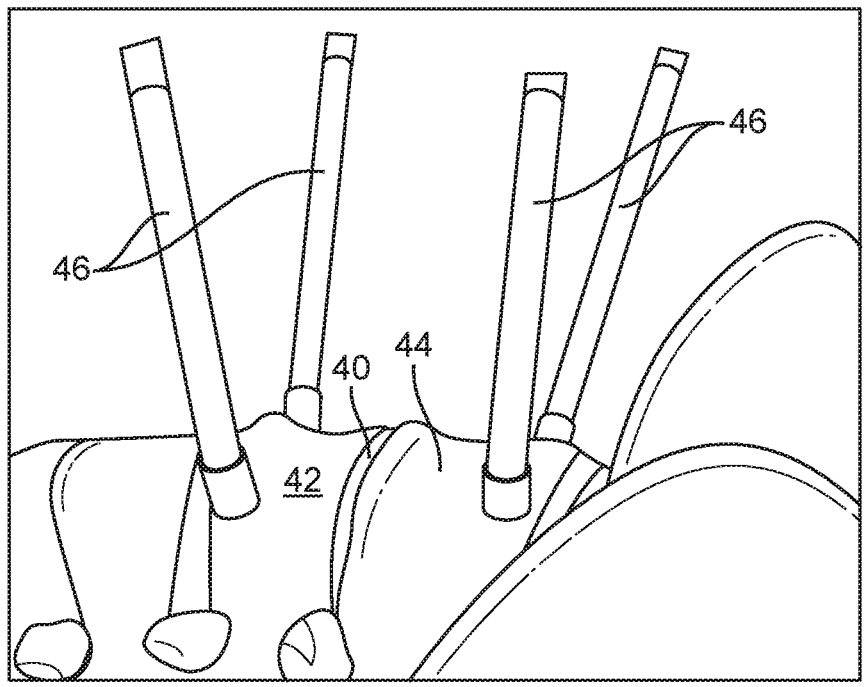
FIG. 3 is a perspective view of a spine with a pair of distractor pins in each of two adjacent vertebrae.

FIG. 3 shows a perspective view of a spine with two adjacent vertebrae 42, 44 and a collapsed disc space 40 located there between. Four distractor pins 46 have been inserted into the two vertebrae in preparation for attachment of the robotic distractor.

Figure 4:
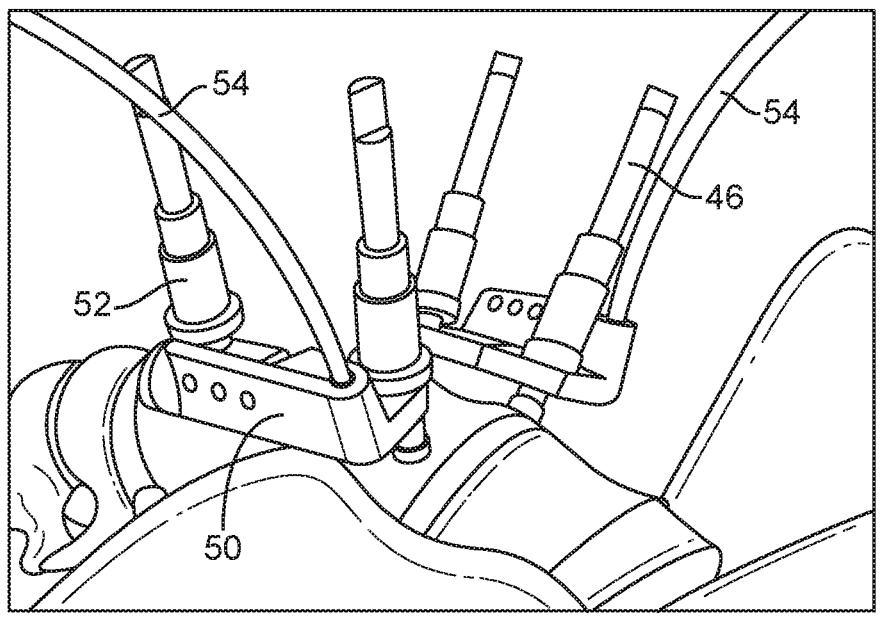
FIG. 4 is a perspective view of a robotic dual action distractor attached to the distractor pins of FIG. 3.

FIG. 4 shows a perspective view of the spine with two robot controlled distractors 50 attached to the distractor pins 46 one either side of the vertebrae midline.

The robot controlled distractors 50 as shown are hydraulic operated telescoping distractors which are supplied with a fluid through the tubing 54. The distractors 50 are separately hydraulically powered telescoping systems that separate and hold apart vertebral bodies in the spinal column during surgery. The robot controlled distractors 50 are each individually controlled and provide independently incremental controlled pressure for distraction. Preferably, the danger of over distraction is minimized by providing a maximum distraction pressure for safety. For example, a maximum pressure of 30 bar or 40 bar can be set for the system. This maximum pressure can be correlated to a specific maximum distraction load/force. Excessive force can result in bending or pull out of the distractor pins. The surgeon can also be provided with the option to set a lower maximum pressure depending on the particular circumstances. The two robot controlled distractors 50 allow the balancing of the two sides of the vertebrae to equalize the distraction. Distraction on the two sides can be balanced by distance (displacement) between the vertebrae or by force.

The amount of desirable distraction force can be controlled or adjusted based on a plurality of different factors including age, gender, neck size and the like. A typical distraction force selected ranges from about 5-15 pounds, preferably about 7-10 pounds.

Although hydraulic distractors have been described herein other types of distractors can also be used including pneumatic distractors, electro-mechanical distractors or mechanical distractors. Alternatively, instead of placing one or more distractors between distractor pins on adjacent vertebrae, multiple robot end effectors can be attached directly to the distractor pins, screws or pegs in place of a distraction mechanism. One example of a hydraulic distractor for the spine is the OrtoWell distractor.

The distractors can be designed to control a force applied between the vertebrae or control a distance between the vertebrae or both. In order to control the distraction based on a distance between the vertebrae, the location of the two vertebrae can be tracked in a 3D model with an imaging system or with the robot controlled distractor its self during surgery. In order to create a 3D model for imaging the vertebrae, imaging will be performed as described in further detail below and may include imaging with X-ray, CT scan, MRI, photographs, infrared camera images or a combination of these methods. Position data for the positions of the first and second vertebrae are generated from the 3D model and stored in a computing system. An alternative method of collecting position data for the positions of the first and second vertebrae would be to include either active or passive sensors (arrays) on the distractor pins themselves. Then as the first and second vertebrae are distracted, the 3D model can be updated automatically.

Imaging Systems

The methods of creation of the 3D model of the vertebrae and location of and tracking of the vertebrae described herein are examples of the systems that may be used. The surgical methods are not meant to be limited to any particular imaging methods or systems and bone tracking methods. The imaging system generates a 3D model of at least the vertebrae above and below the natural disc to be replaced and can also generate a 3D model of additional anatomic structures. This 3D model can be based on a number of different imaging modalities including imaging with X-ray, CT scan, Mill, photograph or a combination of these methods. The images can be taken preoperatively, intraoperatively or a combination thereof.

In one example, a preliminary 3D model of the anatomical area for surgery is created from preoperative CT scan data. Software or the surgeon can use the preliminary 3D model to make a preliminary determination of the intervertebral disc prosthesis to be selected. This preoperative planning can be used to reduce actual surgery time by having an increased chance of selecting the correct disc in a first try. Once the patient is in surgery, markers are attached to the vertebrae above and below the natural disc to be replaced to allow precise identification of the position and orientation of both of the vertebrae throughout surgery. The 3D model is updated with intraoperative fluoroscopic image data or other image data of the vertebrae having the markers to allow real time 3D tracking of the precise position of the vertebrae throughout surgery.

A number of different types of 3D imaging markers are known to be used in surgical robotics. Radiopaque surgical markers can include those that are affixed to bone by screws, pins, adhesives or the like. The radiopaque surgical markers can include a single three dimensional marker for each vertebrae or multiple (preferably three) smaller point type markers. One example of a three dimensional marker for use in determining the position of a bone includes a pin for affixing the marker to the bone and a set of three small radiopaque balls arranged in a triangular configuration like a three headed pin. Preferably, the radiopaque markers are small enough to not get in the way of the surgical procedure, yet large enough to trackable by the imaging system and be easily located for removal after completion of the procedure. Where small markers are used, they may be inserted robotically and/or removed robotically following the procedure to reduce surgery time and incision size. It is also possible to perform the surgical method without any surgical markers, but by registering and tracking anatomical features or mapping of bone surfaces. Alternatively, passive markers, arranged much the same way as the radiopaque markers described above can be tracked by cameras. One such system used infrared reflective fiducials.

The radiopaque markers, mapped bone surfaces or registration of anatomical features allows the imaging system to identify positions of first and second vertebrae and generate and store position data for the positions of the first and second vertebrae in a computing system which transmits this information to a robot control system. The positions of the first and second vertebrae determined from the 3D model of first and second vertebrae at a location of a disc to be replaced from pre-operative and/or intraoperative imaging techniques are used in the subsequent surgery including during the steps of distraction of the disc space, selection of the disc prosthesis and insertion of the disc prosthesis. Preferably, the imaging system will continuously verify the positions of the first and second vertebrae throughout the step of robotically distracting the vertebrae.

The imaging system used can be any of the existing image guided surgery systems.

Selecting Discs

The selection of a disc appropriate for the patient can be performed either in the traditional manual manner by inserting multiple trial discs, in a robot assisted manner by insertion of trial discs with a robot, or in a virtual manner. The traditional manual manner involves beginning by inserting a first size trial and reviewing the fit both manually and by X-ray and then switching trials until the desired fit is confirmed. Usually the manual fitting process begins with inserting a small size trial implant and sequentially moving to larger sized trial implants until an appropriate fit is determined visually, by tactile feel and/or via X-ray. Implants with various lordosis angles may also be tested if available.

A robotic assisted disc selection process uses a robot arm to save time in inserting multiple trial discs of different sizes (height, footprint and/or lordosis) to the same location between the vertebrae and adjusting the size and fit until an optimal fit is achieved. This robotic assisted disc selection process is described further in U.S. Provisional Patent Application No. 62/735,701 filed Sep. 24, 2018 and titled "Robot Assisted Intervertebral Disc Prosthesis Selection and Implantation System and Method" and in U.S. patent application No. 16/578,949 with the same title filed on even date herewith, both of which are incorporated herein by reference. Whether the disc prosthesis is selected manually or by robotic assistance, the robotic distraction system is used throughout the disc selection process to control the spacing and alignment of the vertebrae.

One example of a method for imaging the anatomy of the spine and automatically selecting a spinal implant based on the imaging data is describe in U.S. Pat. No. 7,542,791. When such an imaging modality is used prior to robotic distraction, the robotic distractor can be programed to distract the disc space to the space required for the selected implant without the traditional manual trial process.

Mobilization of the Disc Space

During the disc selection process, the surgeon often needs to remove or cut anatomical structures which are preventing the disc space from being distracted to a desired size in order to fit the disc prosthesis into the disc space. Where a hydraulic robotic distractor is used, force feedback is available in the form of the hydraulic pressure readings from the distractor. Where a mechanical robotic distractor is used force can be measured to provide feedback to the surgeon and the system to indicate the forces being applied to the vertebrae by the distractor. When high forces are experienced in the distractor or when some set maximum force has been reached, this will indicate to the surgeon that some anatomic structure(s) are preventing distraction. Application of additional force to the distractor above a maximum safe force can cause damage to the anatomy. Therefore, if the maximum safe force has been applied to the vertebrae by the distractor and the disc space has not been opened to a sufficient height to receive a selected implant, it may be necessary for the surgeon to cut a portion of the posterior longitudinal ligament or other restricting anatomical structures to mobilize the disc space. The technique of cutting a posterior longitudinal ligament is called a posterior ligament release and is often performed in cases where the anterior side of the disc space is open while the posterior side does not open due to tightness of the surrounding structures.

Additionally, the disc space is prepared for receiving an implant by removing the natural disc material and shaping the bone. The disc space can be prepared for disc implantation by a robotic or manual system for preparing bone for an intervertebral disc implant. Robotic systems for preparing the bone for an intervertebral disc prosthesis are described further in U.S. Provisional Patent Application No. 62/735,666 filed on Sep. 24, 2018 and titled "Robotic System and Method for Bone Preparation for Intervertebral Disc Prosthesis Implantation" and in U.S. patent application No. 16/578,919 with the same title filed on even date herewith both of which are incorporated herein by reference. As described therein, a robotic bone cutting system can significantly improve accuracy of intervertebral disc prosthesis positioning and thereby reduce the pain and discomfort a patient may experience due to improper disc placement. The robotic bone cutting system can give surgeons confidence in the accuracy of disc positioning, decrease surgery and anesthesia time and reduce blood loss.

Distracting Precisely to a Distance to Fit the Selected Disc

In an intervertebral disc prosthesis implantation procedure using a manual distractor, either over distraction or under distraction can occur with different adverse consequences for the patient. The use of a robotic distractor to precisely match the size of the disc space with the size of the trial or implant to be inserted can eliminate both over distraction and under distraction.

In a traditional manual preparation and insertion of a disc prosthesis a significant amount of force can be applied to the patient's anatomy when using a mallet to impact the trials and/or placement instrument. This impact force is applied to the instrument handle and transmitted to the instrument head or implant and to the anatomy of the patient. This impact can lead to temporary post-surgical inflammation and bruising of tissue surrounding the patient's spine that may require pain medication. By precisely distracting the disc space to receive the trials and implant without significant use of a mallet or slaphammer, the patient's pain can be reduced. The impact forces applied during implant insertion can also lead to abrasive debris coming off the disc prosthesis surfaces which is undesirable. The forgoing disadvantages are those that can be cause by under distraction or a distracted distance between the two vertebrae which is smaller than the height of the instrument or disc prosthesis to be inserted.

Disadvantages also result from over distraction of the disc space to a distance larger than the height of the instrument or disc prosthesis to be inserted or distraction to a height which is larger than the height of a natural healthy disc. Over distraction can cause pain and inflammation due to stretching of the soft tissue surrounding the spinal column, can increase the occurrence of axial symptoms, and/or can excessively pull the nerve root and spinal cord.

The robotic distractor can precisely open the disc space just large enough to receive the intervertebral disc prosthesis or instrument of the selected size. This sizing of the disc space to match the instrument or implant can be measured at one or more of a variety of locations achieving different precision. In the simplest case, the disc space height is measured by the imaging system using the 3D model at the anterior midline of the disc space and this distance is matched to the selected instrument or implant. However, measurement at the midline only can be imprecise where the two sides of the disc space are distracted to different heights. In another system, the robotic distractor in combination with the imaging system is used to distract both sides of the disc space to the same distance and this height is matched to the selected instrument or implant.

The robotic distractor can also operate in multiple dimensions to control both the height of the disc space in the anterior and posterior of the disc space. With a three dimensional robotic distractor, the distractor can be used to distract the posterior portion of the disc space as well as the anterior portion. The three dimensional robotic distractor can also distract lateral sides of the disc space independently to achieve lateral balance.

The robotic distractor system can precisely open the disc space just large enough to receive the intervertebral disc prosthesis in both the anterior and posterior portions of the disc space. In one example, where the disc prosthesis is a lordotic disc having a first anterior height larger than a second posterior height, the robotic distractor can precisely open the disc space just large enough to receive the intervertebral disc prosthesis of the selected size and lordosis in both the anterior and posterior portions of the disc space.

As described herein, the term just large enough to receive the intervertebral disc prosthesis or instrument is intended to mean distracting to a space large enough to receive the inserted instrument or implant with less than 0.5 mm clearance or less than 1.0 mm clearance. Where teeth are present, the clearance can be measured from the top of the teeth if the surgeon does not want the teeth to scrape on the vertebrae during insertion. Alternately, the clearance can be measured from the top of the implant not including the teeth if the surgeon elects to allow the teeth to scrape on the vertebrae during insertion.

The 3D model and imaging data generated by the imaging system is preferably used to track the precise location of the two adjacent vertebrae during distraction and determine if the distractor has distracted to the distance just large enough to receive the disc prosthesis. Tracking of the vertebrae can be done by various techniques. In a first technique, radio-opaque markers are affixed to the two vertebrae which can be used to identify the precise positions of the vertebrae. In a second technique, anatomical landmarks are used to provide position information to the computer system. In another technique, electromagnetic transmitter/detectors or passive reflective arrays can be secured to the two vertebrae to automatically update the computing system to any changes in position of the vertebrae. In a further technique, intraoperative camera images are combined with the 3D model data to map the surface of the vertebrae and the location of the mapped surface is tracked via the computing system by continuous review of contemporaneous camera images of the surgical site. Tracking of the precise positions of the two vertebrae is particularly important where instruments are being inserted to prepare the disc space which may alter the positions of the vertebrae. For example, cutters, spreaders, trials, osteotomes, impactors and inserters are all instruments which may alter the positions of the vertebrae.

Computer System for Controlling Robotic Distractor

A computer system controls the robotic distractor to distracting the first and second vertebrae with a computer controlled robotic distractor which precisely opens the disc space just large enough to receive the intervertebral disc prosthesis of the selected size. The computer system can also include the imaging system and size selection software. A computer interface can be displayed on a computer monitor, laptop computer, tablet or other device (e.g. heads-up display or augmented reality) and used in controlling the robotic distractor for optimal distraction and placement of the selected intervertebral disc prosthesis. The interface can include features for disc selection, midline finding, surgical planning, disc space measurement, distraction force monitoring, setting distraction force limits, anterior/posterior distraction monitoring and left/right lateral distraction monitoring. The surgeon can use the computer interface to make and/or adjust a surgery plan for robotic distraction of the vertebrae.

Reverse Distraction for Embedding Cleats into Bone

Although the robotic distractor has been described for use in applying a distraction or outward force on the adjacent vertebrae during intervertebral disc prosthesis insertion, an inward force or reverse distraction may also be useful. In a case where a disc prosthesis is provided with teeth or cleats that are intended to be pressed into the bone, the robotic distractor can be used to provide a reverse distraction (compression) force to seat these teeth or cleats. Once the disc prosthesis is placed fully into the disc space and located in a final position, the robotic reverse distraction can be applied to the distractor pins with the robotic distractor.

Example 1

In a first example, as shown in FIG. 4, two robotic distractors are each connected to two pins, one in the first vertebrae and one in the second vertebrae. When the top and bottom pins connected to a single robotic distractor are in a parallel orientation, the telescoping robotic distractor can move the vertebrae away from one another in parallel. The two lateral sides of the disc space can also be distracted independently to achieve left/right lateral balanced distraction.

Example 2

In a second example, the pins are inserted into the vertebrae substantially as shown in FIGS. 3 and 4, however, the two pins in the upper vertebrae are attached in a fixed manner to a first robot end effector and the two pins in the lower vertebrae are attached in a fixed manner to an end effector of a second robot. Each of the robots is able to control the motion of the connected vertebrae in three dimensions. Thus, the robots can be used to articulate the vertebrae with respect to one another as well as adjust the distance between the vertebrae. The robotic distractor attached in this manner can cause articulation of the vertebrae in both the anterior/posterior direction and the left/right lateral direction to achieve a desired spacing for insertion of the instruments and implants. The robot can be provided with force feedback to prevent over torque of the pins causing pull out of the pins and/or fracture of the vertebrae.

In this example, high forces may be applied to the pins. In addition to force limitation and force feedback, pin modifications may be employed to distribute forces including longer threaded pins entering further into the vertebrae, larger diameter pins or pins with flanges which about the outer bone surfaces to distribute forces.

Example 3

In a third example, the pins are inserted into the vertebrae substantially as shown in FIG. 1, and the pin in the upper vertebrae is attached in a fixed manner to a first robot end effector and the pin in the lower vertebrae is attached in a fixed manner to an end effector of a second robot. Each of the robots is able to control the motion of the connected vertebrae to achieve both distraction and anterior/posterior rotation or articulation. In this example, the distribution of forces and protection from high forces with longer pins, larger pins, flanges or force feedback or monitoring can be used due to the high forces which can occur with a single pin per vertebrae. The force feedback spreader described in Example 4 below can also be used in conjunction with this example or any of the other examples to further mitigate potential excessive force on pins.

Example 4

In a fourth example, a robotic force feedback spreader is provided either alone or in combination with a robotic distraction system. The force feedback spreader includes a pair of paddles shaped for insertion into the disc space between the vertebrae. The robotic spreader applies a controllable distraction force to the paddles to open the disc space. The robotic spreader is particularly useful in between trial instrument insertion steps to provide additional distraction at a posterior portion of the disc space or on a particular side of the disc space. The robotic spreader can be controlled by a surgeon interface through which the surgeon indicates a location for additional distraction on a 3D model and the distraction force to be applied. The robotic spreader paddles are preferably significantly smaller than the width of the vertebral bodies so that they can be used to distract a single side of the vertebral space at one time. For example, the paddles can have a width of about 2-6 mm and can be connected to a scissor mechanism which is controlled by the robot to both move to the precise distraction site and to perform precise distraction to a particular force or distance as prescribed by the surgeon or by a surgical plan.

Interbody Fusion Procedures

Although the robotic surgical distraction systems and methods have been described for use in distraction of vertebrae to accommodate an intervertebral disc prosthesis, the systems and methods described herein may also be used for improved distraction for optimal performance of other spinal implants including interbody fusion devices, interspinous spacers, vertebral body replacements. The robotic distraction systems and methods can be used to assist the surgeon in preventing potential over or under distraction in the placement of these other implants and selection of implants of an appropriate height to fit in the distracted disc space.

Modification of the above-described assemblies and methods for carrying out the invention, combinations between different variations as practicable, and variations of aspects of the invention that are obvious to those of skill in the art are intended to be within the scope of the invention disclosure.

What is claimed is:

1. A surgical method for distraction of a disc space for implantation of an intervertebral disc prosthesis, the method comprising:
    identifying positions of first and second vertebrae and generating and storing a 3D model of the first and second vertebrae in a computing system;
    determining a size of an intervertebral disc prosthesis to be implanted between the first and second vertebrae;
    inserting distractor pins in the first and second vertebrae in a known trajectory;
    distracting the first and second vertebrae with a computer controlled robotic distractor which precisely opens the disc space just large enough to receive the intervertebral disc prosthesis of the selected size.

2. A surgical method of claim 1, wherein the step of determining the size of the intervertebral disc prosthesis is performed via image analysis.

3. A surgical method of claim 1, wherein the step of determining the size of the intervertebral disc prosthesis is performed manually by a surgeon.

4. A surgical method of claim 1, wherein the step of determining the size of the intervertebral disc prosthesis is performed robotically.

5. A surgical method of claim 1, wherein the step of inserting distractor pins is performed manually by a surgeon.

6. A surgical method of claim 1, wherein the step of inserting distractor pins is performed robotically.

7. A surgical method of claim 1, wherein the step of inserting distractor pins includes inserting two distractor pins in each of the first and second vertebrae.

8. A surgical method of claim 1, wherein an initial distraction is performed before the step of determining a size of an intervertebral disc prosthesis.

9. A surgical method of claim 1, further comprising inserting an intervertebral disc prosthesis into the disc space.

10. A surgical method of claim 1, wherein the intervertebral disc prosthesis is inserted into the disc space without the use of an impacting instrument.

11. A surgical method of claim 1, wherein the step of distracting distracts two lateral sides of the disc space independently.

12. A surgical method of claim 1, wherein the step of distracting independently controls distraction of anterior and posterior edges of the disc space.

13. A surgical method of claim 1, wherein a maximum distraction force is set.

14. A surgical method of claim 13, wherein the maximum distraction force is set by the surgeon.

15. A surgical method of claim 13, wherein the maximum distraction force is used to determine the amount of allowable distraction.

* * * * *